United States Patent
Urich et al.

(10) Patent No.: US 8,753,323 B2
(45) Date of Patent: *Jun. 17, 2014

(54) VACUUM SURGE SUPPRESSOR FOR SURGICAL ASPIRATION SYSTEMS

(75) Inventors: Alex Urich, Rancho Santa Margarita, CA (US); Armand Maaskamp, Napa, CA (US)

(73) Assignee: Dana, LLC., Napa, CA (US)

( * ) Notice: Subject to any disclaimer, the term of this patent is extended or adjusted under 35 U.S.C. 154(b) by 310 days.

This patent is subject to a terminal disclaimer.

(21) Appl. No.: 13/159,363

(22) Filed: Jun. 13, 2011

(65) Prior Publication Data
US 2011/0257614 A1    Oct. 20, 2011

Related U.S. Application Data

(63) Continuation-in-part of application No. 13/019,972, filed on Feb. 2, 2011, now Pat. No. 8,372,038, which is a continuation of application No. 12/109,586, filed on Apr. 25, 2008, now Pat. No. 7,914,482.

(60) Provisional application No. 60/934,497, filed on Jun. 13, 2007.

(51) Int. Cl.
  *A61M 1/00*   (2006.01)
  *A61B 17/3205*   (2006.01)

(52) U.S. Cl.
  USPC .............................. 604/320; 604/65; 606/115

(58) Field of Classification Search
  USPC ................................... 604/320, 541; 606/115
  See application file for complete search history.

(56) References Cited

U.S. PATENT DOCUMENTS

| | | | | |
|---|---|---|---|---|
| 1,781,366 A | * | 11/1930 | Campula | 137/513.3 |
| 2,676,613 A | * | 4/1954 | Baxter | 137/513.3 |
| 3,812,855 A | * | 5/1974 | Banko | 604/31 |
| 3,920,014 A | * | 11/1975 | Banko | 604/31 |
| 4,065,093 A | * | 12/1977 | Phillips | 251/6 |
| 4,141,379 A | * | 2/1979 | Manske | 137/496 |
| 4,393,879 A | * | 7/1983 | Milgrom | 600/571 |
| 4,832,685 A | * | 5/1989 | Haines | 604/30 |
| 4,921,477 A | * | 5/1990 | Davis | 604/22 |
| 5,106,367 A | * | 4/1992 | Ureche et al. | 604/30 |
| 5,476,448 A | * | 12/1995 | Urich | 604/22 |
| 5,562,612 A | * | 10/1996 | Fox | 604/27 |
| 5,766,146 A | * | 6/1998 | Barwick, Jr. | 604/28 |
| 5,807,353 A | * | 9/1998 | Schmitz | 604/264 |
| 6,149,633 A | * | 11/2000 | Maaskamp | 604/317 |
| 6,425,883 B1 | * | 7/2002 | Urich et al. | 604/119 |
| 6,599,271 B1 | * | 7/2003 | Easley | 604/119 |

(Continued)

*Primary Examiner* — Melanie Hand
*Assistant Examiner* — Paula Craig

(57) ABSTRACT

An apparatus and method to suppress vacuum surges in a surgical aspiration system is disclosed and claimed. A vacuum surge suppressor includes a first fluid path for coupling to a surgical instrument, and a filter attached to the first fluid path. A flow restrictor is coupled to the filter with the filter disposed upstream of the flow restrictor. The filter defines a filter longitudinal axis that may be oriented vertically with respect to gravity, so that a downstream direction at the filter is upwards. The vacuum surge suppressor also includes a second fluid path for coupling to a vacuum pump. The second fluid path is connected to the flow restrictor and disposed downstream of the flow restrictor. A third fluid path is coupled to the filter and is connected to the second fluid path, bypassing the flow restrictor. A valve in the third fluid path selectively obstructs or permits flow in the third fluid path.

20 Claims, 4 Drawing Sheets

(56) References Cited

U.S. PATENT DOCUMENTS

| | | | |
|---|---|---|---|
| 6,780,166 B2 * | 8/2004 | Kanda et al. | 604/31 |
| 7,083,591 B2 * | 8/2006 | Cionni | 604/31 |
| 7,217,257 B2 * | 5/2007 | Cull et al. | 604/118 |
| 7,914,482 B2 * | 3/2011 | Urich et al. | 604/65 |
| 8,162,919 B2 * | 4/2012 | Cull et al. | 604/505 |
| 8,372,038 B2 * | 2/2013 | Urich et al. | 604/119 |
| 8,617,106 B2 * | 12/2013 | Zacharias | 604/119 |
| 2002/0022810 A1 * | 2/2002 | Urich | 604/317 |
| 2002/0128560 A1 * | 9/2002 | Urich | 600/500 |
| 2003/0078591 A1 * | 4/2003 | Barrett | 606/107 |
| 2004/0039351 A1 * | 2/2004 | Barrett | 604/272 |
| 2005/0054971 A1 * | 3/2005 | Steen et al. | 604/22 |
| 2005/0113741 A1 * | 5/2005 | Huang et al. | 604/35 |
| 2006/0173426 A1 * | 8/2006 | Urich et al. | 604/317 |
| 2006/0224163 A1 * | 10/2006 | Sutton | 606/107 |
| 2007/0129694 A1 * | 6/2007 | Opie et al. | 604/313 |
| 2008/0294095 A1 * | 11/2008 | Zacharias | 604/65 |
| 2010/0185150 A1 * | 7/2010 | Zacharias | 604/119 |
| 2010/0292631 A1 * | 11/2010 | Holden | 604/22 |
| 2010/0305496 A1 * | 12/2010 | Kuebler et al. | 604/22 |

* cited by examiner

VACUUM SURGE SUPPRESSOR FOR SURGICAL ASPIRATION SYSTEMS

CROSS-REFERENCE TO RELATED APPLICATIONS

This application claims benefit under 35 U.S.C. §120 as a continuation-in-part of pending U.S. patent application Ser. No. 13/019,972, entitled "VACUUM SURGE SUPPRESSOR FOR SURGICAL ASPIRATION SYSTEMS," filed on Feb. 2, 2011, hereby incorporated by reference, which claims benefit under 35 U.S.C. §120 as a continuation of pending U.S. patent application Ser. No. 12/109,586, entitled "VACUUM SURGE SUPPRESSOR FOR SURGICAL ASPIRATION SYSTEMS," filed on Apr. 25, 2008, hereby incorporated by reference, and which claims priority under 35 U.S.C. §119(e) to U.S. Provisional Application No. 60/934,497, entitled "VACUUM SURGE SUPRESSOR WITH ADJUSTABLE FLOW PATH," filed on Jun. 13, 2007, also hereby incorporated by reference.

FIELD OF THE INVENTION

The present invention relates generally to the field of medical devices used in surgery, and more particularly to aspiration systems used in surgery.

BACKGROUND

Various contemporary surgical procedures require aspiration of fluids that may contain solid or semi-solid tissue or other debris. In many cases, the fluids may need to be aspirated from a body cavity such as the lens capsule of the eye or a cavity in a joint such as the shoulder or the knee. It is typically desirable to maintain an ambient or a super-ambient pressure within the body cavity during such surgical procedures.

For example, the lens of a human eye may develop a catacteous condition that affects a patient's vision. Catacteous lenses are sometimes removed and replaced in a procedure commonly referred to as phacoemulsification. Phacoemulsification procedures are typically performed with an ultrasonically driven hand piece that is used to break the lens within the lens capsule of the eye. The broken lens is removed through an aspiration line that is coupled to the hand piece and protrudes into the lens capsule. The hand piece has a tip that is inserted through an incision in the cornea. The hand piece typically contains a number of ultrasonic transducers that convert electrical power into a mechanical oscillating movement of the tip. The distal end of the tip has an opening that is in fluid communication with the aspiration line. The distal end of the tip also has a sleeve that has an opening in fluid communication with an irrigation line. The irrigation line is typically connected to a bottle that can provide irrigation fluid to the surgical site. The oscillating movement of the tip breaks the lens into small pieces. The lens pieces and irrigation fluid are drawn into the aspiration line through the opening of the tip.

Phacoemulsification is more likely to be successful if ambient or super-ambient pressure can be maintained within the lens capsule and the anterior chamber of the eye during the procedure. However, vacuum surges can be created when the aspiration line is momentarily obstructed by solid or semi-solid tissue. Such vacuum surges can lead to transient aspiration flow rates through the aspiration line that substantially exceed the flow rate through the irrigation line and thereby cause a sub-ambient pressure to be momentarily applied to the surrounding tissue. The momentary sub-ambient pressure condition may cause an undesirable collapse of the anterior chamber of the eye, undesirable damage to the posterior aspect of the lens capsule of the eye, and/or endothelium cells to be undesirably drawn away from the cornea and towards the distal end the tip of the hand piece. On the other hand, too high an irrigation flow rate may undesirably move endothelium cells away from the cornea, or undesirably cause endothelium cells to be aspirated out of the eye.

Conventional phacoemulsification procedures are typically performed using a vacuum pressure of about 250 mmHg. There is a desire to increase the vacuum pressure to assist in aspirating larger pieces of the lens. Aspirating larger pieces would lower the amount of ultrasonic work that must be performed on the eye. Lowering the ultrasonic work would be desirable because ultrasound can irritate the eye. Consequently, there is a desire to create vacuums up to 500 mmHg to improve aspiration and reduce the amount of ultrasound delivered to the cornea. However, such higher pressures exacerbate the surgical risks associated with vacuum surges.

Also for example, some orthopedic medical procedures produce particles or other debris that must be removed from a cavity within a joint such as in the shoulder or knee. To remove such particles the surgeon may couple an aspiration tube to the surgical site. The aspiration tube, which pulls the debris from the body, is typically connected to a canister, which is connected to a suction tube connected to wall suction. To ensure that the surgical site is properly distended during surgery, relatively large quantities of irrigation fluid are typically introduced to the body to continuously irrigate the surgical site, and an infusion pump is typically required to offset the high flow created by the hospital vacuum line. The introduction of such amounts of irrigation fluid into the body can cause undesirable or excessive extravagation of irrigation fluid into the surrounding tissue. Also, vacuum surges can be created when the suction line is obstructed by solid or semi-solid tissue. Such vacuum surges can lead to transient aspiration flow rates through the hospital vacuum line that substantially exceed the flow rate of irrigation fluid and thereby cause a sub-ambient pressure to be momentarily applied to the surrounding tissue. The momentary sub-ambient pressure condition may cause partial collapse of the body cavity, damage to tissue near the distal end of the aspiration tube, and/or undesired tissue or fluid to be drawn towards the distal end of the aspiration tube.

Surgical aspiration systems may be designed to allow the surgeon to temporarily reverse the direction of aspiration flow by depressing a reflux bulb attached to the system. The surgeon may do this, for example, if tissue is drawn towards the distal tip of the aspiration tube or hand piece that the surgeon does not desired to be drawn (e.g. tissue that the surgeon does not want to be damaged by the distal tip). The surgeon may also initiate reflux to clear or dislodge an occlusion at the distal tip of the aspiration tube or hand piece.

Contemporary flow restrictors can limit the vacuum surges within the aspiration system, but only when the vacuum created by the vacuum pump is limited to a level that is safe in consideration of the diameter and length of that flow restrictor. For example, considering the typical dimensions of needles and tubings used in ophthalmology, the flow that would be generated by a 500 mmHg vacuum is in excess of 250 cc/min, which could undesirably completely collapse an eye. Therefore, prior art systems that use a venturi pump must operate modest vacuum levels, e.g. below 200 mmHg unless very small needles are used. Such modest vacuum levels significantly limit the available un-occluded flow in such systems. Therefore, such flow restrictors are typically not used with peristaltic pumps that will significantly increase the pressure difference in response to an occlusion of the aspiration tip. The absence of pressure rise in response to occlusion in the contemporary aspiration systems limits their ability to aspirate large tissue particles. Also, an in-line flow restrictor may reduce the maximum flow rate in the absence of occlusion, even when the surgeon would prefer a higher flow rate to draw certain tissue towards the distal end of the tip (rather than moving the distal end of the tip towards the tissue). Also, an in-line flow restrictor can undesirably reduce the maximum reflux flow rate.

Therefore, it would be desirable to provide a surgical aspiration system that maintains an ambient or super-ambient pressure within a body cavity during a surgical procedure by limiting vacuum surges in the system. For example, it would be desirable to provide an aspiration system that is configured such that the flow rate out of the body cavity through the aspiration line does not greatly, or for a prolonged period, exceed the flow rate into the body cavity. In cataract surgery, for example, aspiration flow should be sufficient to quickly engage and aspirate lens particles from the eye, however in the event of an occlusion the high vacuum created in the aspiration line may temporarily produce too high a flow which could collapse the eye. Therefore, it would also be desirable to provide a surgical aspiration system that functions safely with limited or reduced flow rate of irrigation fluid through the irrigation line. It would also be desirable to provide an aspiration system that can safely take advantage of the use of a peristaltic pump (or another pump type that can significantly increase the relative vacuum response to an occlusion). It would also be desirable to provide an aspiration system that would allow a high aspiration flow rate in the absence of an occlusion, and a high reflux flow rate when needed by the surgeon.

SUMMARY

An apparatus and method to suppress vacuum surges in a surgical aspiration system is disclosed and claimed. A vacuum surge suppressor includes a first fluid path for coupling to a surgical instrument, and a filter attached to the first fluid path. A flow restrictor is coupled to the filter with the filter disposed upstream of the flow restrictor. The filter defines a filter longitudinal axis that may be oriented vertically with respect to gravity, so that a downstream direction at the filter is upwards. The vacuum surge suppressor also includes a second fluid path for coupling to a vacuum pump. The second fluid path is connected to the flow restrictor and disposed downstream of the flow restrictor. A third fluid path is coupled to the filter and is connected to the second fluid path, bypassing the flow restrictor. A valve in the third fluid path selectively obstructs or permits flow in the third fluid path.

DETAILED DESCRIPTION

Figure 1:
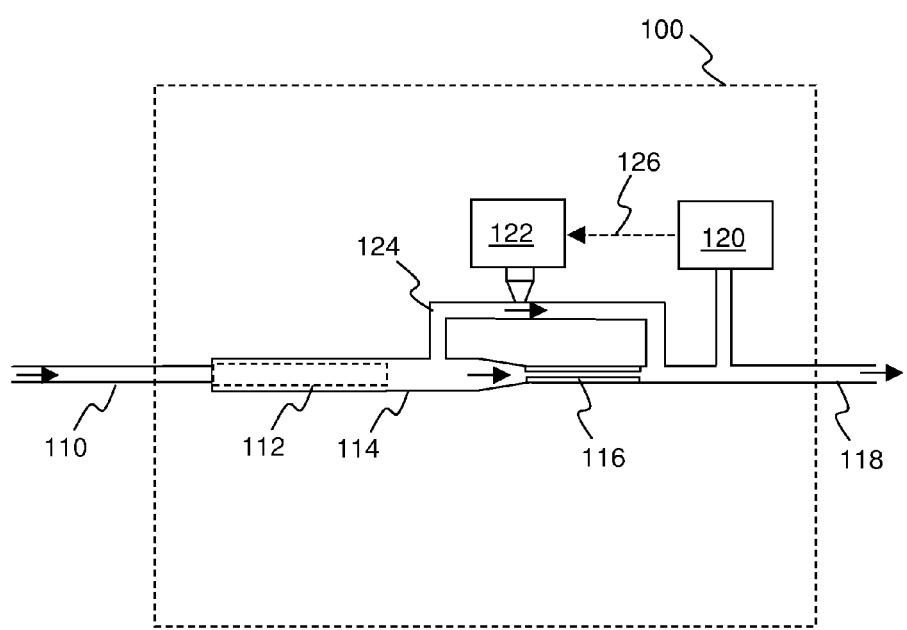
FIG. 1 is a schematic depiction of a vacuum surge suppressor according to an embodiment of the present invention.

FIG. 1 is a schematic depiction of a vacuum surge suppressor 100 according to an embodiment of the present invention. Fluid and solid material from an irrigated surgical site may be aspirated through input tubing 110, also referred to as the "aspiration line." During normal operation, the input tubing 110 would be coupled to a surgical instrument such as a hand piece designed to facilitate surgery in a body cavity (e.g. a phacoemulsification hand piece). Coupling to the surgical instrument can be accomplished by attachment to the surgical instrument or to another fluid pathway that itself is coupled to the surgical instrument. Filter 112, which is depicted in FIG. 1 as being an in-line filter that is disposed in filter housing 114 and coupled to input tubing 110, retains larger particles of the aspirated material such that only small particles can pass through the filter 112.

In the embodiment of FIG. 1, a flow restrictor 116 is disposed downstream of the filter housing 114. The term "downstream" as used herein, does not imply the necessity for any flow or fluid in the system as claimed. Rather, "downstream" is used herein only to indicate a direction to facilitate discussion of the relative position of components within the system, by referring to flow that would occur during periods of normal operation without reflux, and serves the purpose of facilitating such discussion even for systems that are not presently in use and contain no fluid or flow. Likewise, "upstream" means that a component would be normally upstream if installed in an operating system; it does not require any flow or fluid in the vacuum surge suppressor component when it is not installed in an operable system or when an operable system is not operating. The filter housing 114 may have various shapes but is preferably tapered at the entrance into the flow restrictor 116 to reduce the formation of air bubbles. The flow restrictor 116 preferably comprises an orifice defining an orifice inner diameter in the range 0.005 to 0.025 inches and an orifice length in the range 1 to 2 inches. For example, the orifice may be designed to have an inner diameter of 0.010 inches and a length of 1 inch. The orifice preferably has fixed dimensions because it is difficult for an orifice that allows adjustment to achieve the desired precision. For example, a restriction of 0.02 inch diameter will allow 16 times more flow then a 0.01 inch diameter because flow is proportional with the 4th power of diameter.

In the embodiment of FIG. 1, output tubing 118 is disposed downstream of the flow restrictor 116. During normal operation, the output tubing 118 would be coupled to a vacuum pump designed to create a sub-ambient pressure in output tubing 118. Coupling to the vacuum pump can be accomplished by attachment to the vacuum pump or attachment to the output tubing 118 or another fluid pathway that itself is coupled to the output tubing 118. The sub-ambient pressure pumps used in ophthalmic instrumentation are commonly called "vacuum pumps" even though they do not create an absolute vacuum but rather create a pressure that is below ambient pressure but still greater than zero absolute pressure. "Vacuum" is used herein in the relative sense rather than in an absolute sense, so that "vacuum" refers to the magnitude of the pressure difference between ambient pressure and a sub-ambient pressure that corresponds to the vacuum. Therefore, as used herein, vacuum is said to increase when the corresponding sub-ambient pressure falls to a lower absolute pressure value that is further from the ambient pressure, and vacuum is said to decrease when the corresponding sub-ambient pressure rises to a higher absolute value that is closer to ambient pressure.

In the embodiment of FIG. 1, for example, a venturi pump may be coupled to output tubing 118 to create a relatively constant vacuum therein. Alternatively, for example, a peristaltic pump may be coupled to output tubing 118 to create a vacuum will increase if/when the flow is occluded. A pressure sensor 120 coupled to the output tubing 118 may sense the vacuum in the output tubing 118. For example, the pressure sensor 120 may be attached to the output tubing 118 as shown in FIG. 1. The pressure sensor 120 is preferably a transducer that is capable of sensing the path internal pressure in the output tubing 118, and providing an electrical potential, signal, or other electrical characteristic (e.g. electrical impedance) that is responsive to such path internal pressure. The pressure sensor may be designed to sense relative pressure rather than absolute pressure, for example providing an electrical potential, signal, or other electrical characteristic that is indicative of the vacuum in the output tubing 118.

In the embodiment of FIG. 1, bypass tubing 124 is coupled to the filter housing 114 and to the output tubing 118, in a way that bypasses the flow restrictor 116. Bypass tubing 124 may be coupled to the filter housing 114 by being connected to the filter housing 114, as shown in FIG. 1, or alternatively by being connected to a fluid path that is itself connected to the filter housing 114. Likewise, bypass tubing 124 may be coupled to the output tubing 118 by being connected to the output tubing 118 as shown in FIG. 1, or alternatively by being connected to a fluid path that is itself connected to the output tubing 118. In either case, under normal operation the bypass tubing 124 carries a flow that bypasses the flow restrictor 116. In the embodiment of FIG. 1, bypass tubing 124 need not be "rigid" tubing but is preferably flexible tubing that does not collapse in response to sub-ambient pressure at sea level. The bypass tubing 124 may, for example, comprise so-called hard silicon tubing.

Moreover, bypass tubing 124 may be and/or may include a valve 122 that can substantially interrupt the flow in bypass tubing 124 in response to the path internal pressure of the output tubing 118. For example, the valve 122 may be a discrete automated valve (e.g. a solenoid-driven valve) that is responsive to an output 126 of the pressure sensor 120. The output 126 of the pressure sensor 120 may be conditioned and/or amplified by other conventional circuitry. For example, if the pressure sensor 120 provides a time-varying voltage that is responsive to path internal pressure, such time-varying voltage may be amplified by an amplifier and/or conditioned by a logic circuit to create the output 126. Optionally, the amplifier may be an inverting amplifier, for example if it is desired that decreasing relative pressure (i.e. increasing vacuum) would correspond to increasing voltages. Also for example, if the pressure sensor 120 provides a time-varying electrical impedance that is responsive to path internal pressure, such time-varying impedance may be detected by an analog circuit and perhaps by digital sampling, and then be further conditioned by a logic circuit to create the output 126. Such a logic circuit might, for example, provide a constant voltage to valve 122 (e.g. to keep it open if it is a normally closed solenoid valve) and discontinue such (allowing the valve 122 to close) only when the time-varying voltage or impedance exceeds or falls below a certain threshold. Alternatively, the amplification and/or logic circuitry may be included with the valve 122 so that the output 126 that is shown in FIG. 1 corresponds to the raw, unconditioned output of the pressure sensor. In either case, the action of the valve 122 is responsive to the pressure sensed by the pressure sensor 120, by a conventional means.

Figure 2:
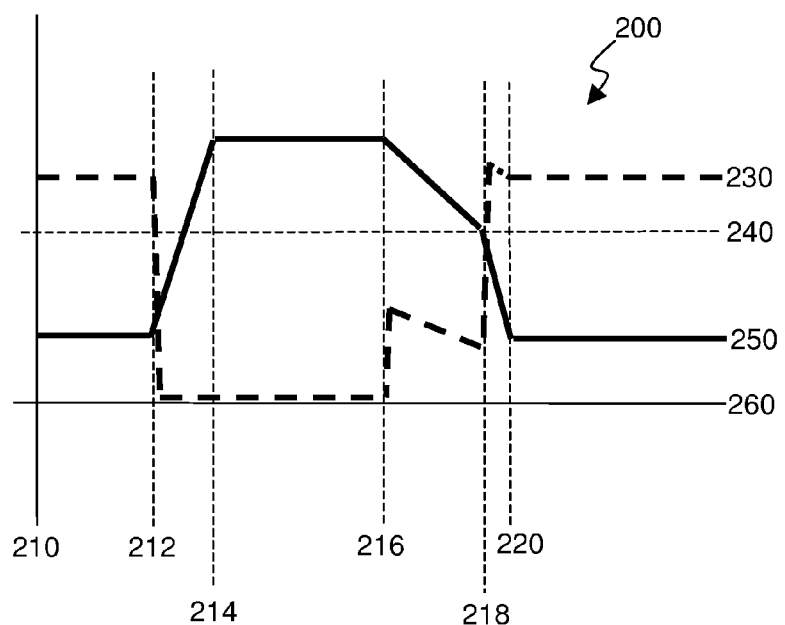
FIG. 2 is an example graph of vacuum and flow versus time according to an embodiment of the present invention.

FIG. 2 is an example graph 200 of vacuum 250 and total flow 230 through output tubing 118, versus time (increasing to the right along time axis 260), to illustrate the manner of operation of an embodiment of the present invention. At the far left side 210 of the graph 200, the vacuum 250 is sensed by sensor 120 to be less than a preset safety threshold 240 (e.g. a vacuum level less than 250 mmHG, such as 200 mmHg), so the valve 122 is kept open and flow passes through bypass tubing 124. The availability of the bypass tubing 124 for flow allows the total flow 230 to be at a high value. Such a high flow condition may be desirable in surgery; for example in phacoemulsification surgery it may be useful to quickly attract lens material into the surgeon's hand piece. Moreover, the availability of open bypass tubing 124 may advantageously facilitate the creation of reflux flow by the surgeon at the surgeon's discretion, without such reflux flow being constrained by the flow restrictor 116.

However, at a later time 212 the flow 230 is occluded (for example by solid material being aspirated into the surgical instrument that is coupled to the input tubing 110), so that the flow 230 becomes zero and the vacuum 250 rapidly increases (assuming that the pump that is coupled to output tubing 118 is a peristaltic pump rather than a venturi pump). At a time between time 212 and time 214, the vacuum 250 is sensed by sensor 120 to have increased above the preset safety threshold 240, so that the valve 122 is closed, blocking flow through the bypass tubing 124 so that subsequent flow must pass through the flow restriction 116. At time 214 the vacuum 250 reaches a maximum that the pump is configured to produce (e.g. 500 mmHg or more). The flow 230 remains nearly zero at this time, however, because the occlusion has not yet passed.

At time 216, the occlusion finally passes so that the vacuum 250 can once again cause flow 230 to rise. Since the vacuum 250 is at a high level, the flow 230 would rise rapidly to a dangerously high level (that could have adverse surgical effects) if not for the valve 122 being closed so that all of the flow 230 must pass through the flow restrictor 116. Instead, the flow 230 only rises to a safe level that is permitted by the flow restrictor 116, though the damping introduced by the flow restrictor 116 may not completely suppress the flow overshoot. Between times 216 and 218, the moderate flow 230 causes the vacuum 250 to diminish until it is sensed by sensor 120 to have fallen below the present safety threshold 240. Then (i.e. at time 218) the valve 122 is re-opened, allowing flow through the bypass tubing 124 so that the total flow 230 rises back to its pre-occlusion high level. The higher flow 230 causes the vacuum 250 to diminish further until, at time 220, it reaches its pre-occlusion low level.

Thus, in the manner shown in FIG. 2, the embodiment of FIG. 1 enables safe transitions from a non-occluded, high-flow, low-vacuum condition, to an occluded, low-flow, high-vacuum condition, and back again. Through the actions of valve 122 and flow restrictor 116, surges in flow due to post-occlusion periods of high vacuum are moderated to prevent adverse surgical effects. In phacoemulsification procedures, for example, such adverse surgical effects may include collapse of the anterior chamber of the eye, undesired aspiration of endothelium cells, and/or damage to the posterior aspect of the lens capsule.

The embodiment of FIG. 1 may employ a venturi pump rather than a peristaltic pump, in which case it preferably also includes vacuum control switches controllable by the surgeon using a foot pedal. One switch may increase the vacuum and the other decrease the vacuum within preset limits. Whereas the range of adjustment typically could not safely exceed 10% in prior art devices, this range may be increased significantly (e.g. 100%) using the embodiment of FIG. 1. For example, if the threshold is set to 250 mmHg, then the surgeon can operate below 250 mmHg with unrestricted flow. However, if/when the surgeon feels that more vacuum is necessary at a certain time he/she can safely raise the vacuum above the threshold up to the highest limit of the pump (e.g. 600 mmHg) in which case the flow will be restricted by flow restrictor 116 of FIG. 1.

Figure 3:
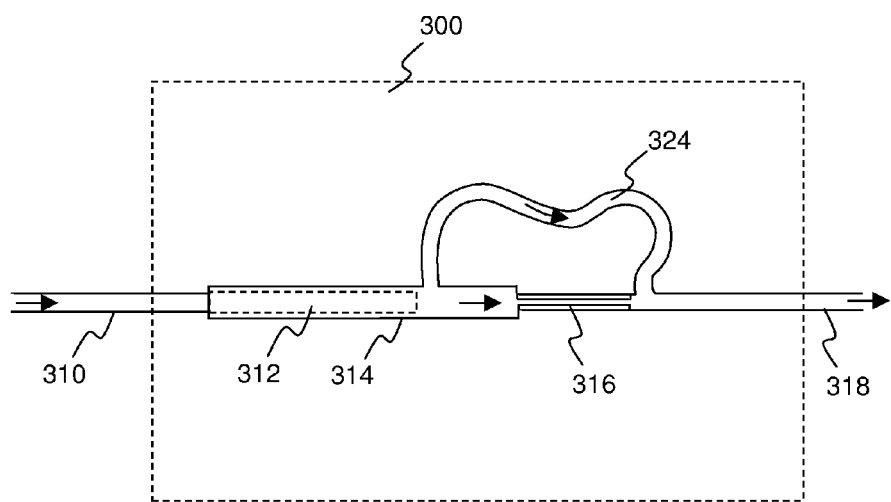
FIG. 3 is a schematic depiction of a vacuum surge suppressor according to another embodiment of the present invention.

FIG. 3 is a schematic depiction of a vacuum surge suppressor 300 according to another embodiment of the present invention. In the embodiment of FIG. 3, input tubing 310 is coupled to filter housing 314, which contains filter 312, and output tubing 318 is coupled to flow restrictor 316. For example, the input tubing 310 may be coupled to filter housing 314 by being attached to filter housing 314, and the output tubing 318 may be coupled to flow restrictor 316 by being attached to flow restrictor 316. The flow restrictor 316 is coupled to filter housing 314, for example by being attached to filter housing 314 or being part of filter housing 314. Bypass tubing 324 is coupled to the filter housing 314 and to the output tubing 318, in a way that bypasses the flow restrictor 316.

In the embodiment of FIG. 3, the bypass tubing 324 comprises collapsible tubing (e.g. thin, collapsible silicone tubing). The collapsible bypass tubing 324 is designed (e.g. by specifying tubing wall thickness) such that the tubing collapses when the vacuum exceeds a preset threshold (e.g. 200 mmHg). In this manner, the collapsible bypass tubing 324 of the embodiment of FIG. 3 serves the combined functions of the pressure sensor 120, the valve 122, and the bypass tubing 124 in the embodiment of FIG. 1. That is, when the collapsible bypass tubing 324 of the embodiment of FIG. 3 collapses, the majority of flow must then pass through the flow restrictor 316 and the system operates in a manner that is similar to that described with reference to FIG. 2. Although the embodiment of FIG. 3 has reduced complexity and cost relative to the embodiment of FIG. 1, the embodiment of FIG. 1 may allow the vacuum threshold 240 to be dynamically changed under software control. The vacuum threshold 240 in the embodiment of FIG. 3 is determined by material properties and so is not easily controlled and may be undesirably affected by environmental conditions such as temperature.

Figure 4:
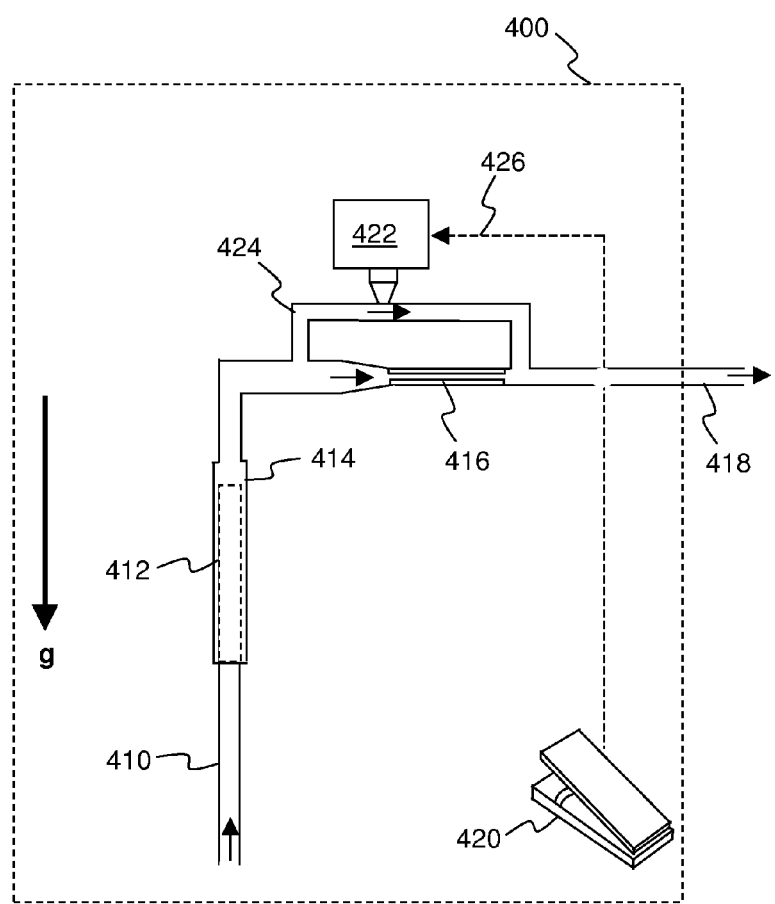
FIG. 4 is a schematic depiction of a vacuum surge suppressor according to another embodiment of the present invention.

FIG. 4 is a schematic depiction of a vacuum surge suppressor 400 according to another embodiment of the present invention. Fluid and solid material from an irrigated surgical site may be aspirated through input tubing 410, also referred to as the "aspiration line." During normal operation, the input tubing 410 would be coupled to a surgical instrument such as a hand piece designed to facilitate surgery in a body cavity (e.g. a phacoemulsification hand piece). Coupling to the surgical instrument can be accomplished by attachment to the surgical instrument or to another fluid pathway that itself is coupled to the surgical instrument.

The embodiment of FIG. 4, includes a filter 412 that is an in-line filter disposed in a filter housing 414 and coupled to input tubing 410. The filter 412 retains larger particles of the aspirated material such that only small particles can pass through the filter 412. Although the direction of gravitational acceleration is not specified in FIGS. 1 and 3 (so that the various elements shown in those figures may have any orientation with respect to gravitational acceleration), the filter housing 414 shown in FIG. 4 is expressly depicted to be oriented vertically with respect to gravitational acceleration g. In certain embodiments, the vertical and upward orientation of the flow through the filter 412 and filter housing 414 increases the likelihood that the filter will fully prime, such that it is less likely for bubbles or packets of air to become trapped inside the filter 412 or the filter housing 414.

In the embodiment of FIG. 4, a flow restrictor 416 is disposed downstream of the filter housing 414. The entrance into the flow restrictor 416 is preferably tapered to reduce the formation of air bubbles. The flow restrictor 416 preferably comprises an orifice defining an orifice inner diameter in the range 0.005 to 0.025 inches and an orifice length in the range 1 to 2 inches. For example, the orifice may be designed to have an inner diameter of 0.010 inches and a length of 1 inch. The orifice preferably has fixed dimensions because it is difficult for an orifice that allows adjustment to achieve the desired precision. For example, a restriction of 0.02 inch diameter will allow 16 times more flow then a 0.01 inch diameter because flow is proportional with the 4th power of diameter.

In the embodiment of FIG. 4, output tubing 418 is disposed downstream of the flow restrictor 416. During normal operation, the output tubing 418 would be coupled to a vacuum pump designed to create a sub-ambient pressure in output tubing 418. Coupling to the vacuum pump can be accomplished by attachment to the vacuum pump or attachment to the output tubing 418 or another fluid pathway that itself is coupled to the output tubing 418. In the embodiment of FIG. 4, for example, a venturi pump may be coupled to output tubing 418 to create a relatively constant vacuum therein. Alternatively, for example, a peristaltic pump may be coupled to output tubing 418 to create a vacuum will increase if/when the flow is occluded.

In the embodiment of FIG. 4, bypass tubing 424 is coupled to the filter housing 414 and to the output tubing 418, in a way that bypasses the flow restrictor 416. Bypass tubing 424 may be coupled to the filter housing 414 by being connected to the filter housing 414, or alternatively by being connected to a fluid path that is itself connected to the filter housing 414, as shown in FIG. 4. Likewise, bypass tubing 424 may be coupled to the output tubing 418 by being connected to the output tubing 418 as shown in FIG. 4, or alternatively by being connected to a fluid path that is itself connected to the output tubing 418. In either case, under normal operation the bypass tubing 424 carries a flow that bypasses the flow restrictor 416. In the embodiment of FIG. 4, bypass tubing 424 need not be "rigid" tubing but is preferably flexible tubing that does not collapse in response to sub-ambient pressure at sea level. The bypass tubing 424 may, for example, comprise so-called hard silicon tubing.

Moreover, bypass tubing 424 may be and/or may include a valve 422 that can substantially interrupt the flow in bypass tubing 424 in response to a command input by the operating physician or surgeon. For example, in the embodiment of FIG. 4, the valve 422 may be a solenoid-driven valve that is responsive to a driving signal 426 that passes through a conventional switch or potentiometer that is manipulated by a conventional foot pedal 420, which is controlled by the operating physician or surgeon. It is also possible for the valve 422 to be controlled by the foot pedal 420 via a conventional mechanical linkage to the foot pedal 420, or via a conventional hydraulic pressure connection to a conventional hydraulic piston at the foot pedal 420.

In certain embodiments of the present invention, such manual control of the valve 422 (e.g. by a surgeon's manipulation of the foot pedal 420) may be preferred to automatic control of the valve 422 in response to the output of a pressure sensor. For example, some surgeons may prefer to use high vacuum for an entire surgical procedure, while others may prefer to use low vacuum but high flow during the entire surgical procedure. Manual control of the valve 422 (e.g. via foot pedal 420) may satisfy either preference, so that the same device might be used, advantageously reducing inventory.

Alternatively, in certain embodiments of the present invention, the foot pedal 420 may be used by the surgeon or operating physician to change the state of valve 422 at different phases of the same surgical procedure. For example, in phacoemulsification, the extraction of the eye lens may have three phases in which a different vacuum level may be desired. In the first phase, a low vacuum and high flow may be preferred, while in the second phase a high vacuum may be preferred, and then in the third phase a moderate vacuum may be preferred.

In the foregoing specification, the invention is described with reference to specific exemplary embodiments, but those skilled in the art will recognize that the invention is not limited to those. It is contemplated that various features and aspects of the invention may be used individually or jointly and possibly in a different environment or application. The specification and drawings are, accordingly, to be regarded as illustrative and exemplary rather than restrictive. For example, the word "preferably," and the phrase "preferably but not necessarily," are used synonymously herein to consistently include the meaning of "not necessarily" or optionally. "Comprising," "including," and "having," are intended to be open-ended terms.

What is claimed is:

1. A vacuum surge suppressor, for a surgical aspiration system that includes a surgical instrument and a vacuum pump, the vacuum surge suppressor comprising:
    a first fluid path for coupling to the surgical instrument;
    a filter attached to the first fluid path, the filter defining a filter longitudinal axis that is oriented vertically with respect to gravity so that a downstream direction at the filter is upwards;
    a flow restrictor coupled to the filter, the flow restrictor comprising an orifice defining a fixed orifice inner diameter in the range 0.005 to 0.025 inches and a fixed orifice length in the range 1 to 2 inches, the filter being disposed upstream of the flow restrictor;
    a second fluid path for coupling to the vacuum pump, the second fluid path connected to the flow restrictor and disposed downstream of the flow restrictor, the second fluid path defining a path internal pressure;
    a third fluid path coupled to the filter and connected to the second fluid path, bypassing the flow restrictor; and
    a valve in the third fluid path that obstructs flow in the third fluid path in response to the path internal pressure.

2. The vacuum surge suppressor of claim 1 wherein the first fluid path comprises a tube adapted to be connected to a corresponding tube of the surgical instrument.

3. The vacuum surge suppressor of claim 1 wherein the second fluid path comprises a tube adapted to be connected to a corresponding tube of the vacuum pump.

4. The vacuum surge suppressor of claim 1 wherein the filter includes a filter housing, and the first fluid path is connected to the filter housing.

5. The vacuum surge suppressor of claim 1 wherein the filter includes a filter housing, and the flow restrictor is connected to the filter housing.

6. The vacuum surge suppressor of claim 5 wherein the third fluid path is connected to the filter housing.

7. The vacuum surge suppressor of claim 1 further comprising a pressure sensor capable of sensing the path internal pressure, and wherein the valve is a discrete automated valve that is responsive to an output of the pressure sensor.

8. The vacuum surge suppressor of claim 7 wherein the third fluid path comprises a rigid plastic tube.

9. The vacuum surge suppressor of claim 7 wherein the discrete automated valve is a solenoid driven valve.

10. The vacuum surge suppressor of claim 1 wherein the filter is an in-line filter.

11. A vacuum surge suppressor, for a surgical aspiration system that includes a surgical instrument and a vacuum pump, the vacuum surge suppressor comprising:
    a first fluid path for coupling to the surgical instrument;
    a filter attached to the first fluid path;
    a flow restrictor coupled to the filter, the flow restrictor comprising an orifice defining a fixed orifice inner diameter in the range 0.005 to 0.025 inches and a fixed orifice length in the range 1 to 2 inches, the filter being disposed upstream of the flow restrictor;
    a second fluid path for coupling to the vacuum pump, the second fluid path connected to the flow restrictor and disposed downstream of the flow restrictor;
    a third fluid path coupled to the filter and connected to the second fluid path, bypassing the flow restrictor; and
    a valve in the third fluid path that selectively obstructs or permits flow in the third fluid path in response to a human control input.

12. The vacuum surge suppressor of claim 11 wherein the filter includes a filter housing that is oriented vertically with respect to gravity so that a downstream direction at the filter is upwards, and wherein the first fluid path is connected to the filter housing.

13. The vacuum surge suppressor of claim 12 wherein the filter is an in-line filter.

14. The vacuum surge suppressor of claim 11 wherein the valve is a solenoid driven valve.

15. The vacuum surge suppressor of claim 11 wherein the first fluid path comprises a tube adapted to be connected to a corresponding tube of the surgical instrument.

16. The vacuum surge suppressor of claim 11 wherein the second fluid path comprises a tube adapted to be connected to a corresponding tube of the vacuum pump.

17. The vacuum surge suppressor of claim 11 wherein the human control input is administered by a foot pedal.

18. The vacuum surge suppressor of claim 17 wherein the foot pedal is attached to a device selected from the list consisting of a switch, a potentiometer, and a hydraulic piston.

19. A vacuum surge suppressor, for a surgical aspiration system that includes a surgical instrument and a vacuum pump, the vacuum surge suppressor comprising:
    a first fluid path for coupling to the surgical instrument;
    a filter attached to the first fluid path;
    a flow restrictor coupled to the filter, the flow restrictor comprising an orifice defining a fixed orifice inner diameter in the range 0.005 to 0.025 inches and a fixed orifice length in the range 1 to 2 inches, the filter being disposed upstream of the flow restrictor;
    a second fluid path for coupling to the vacuum pump, the second fluid path connected to the flow restrictor and disposed downstream of the flow restrictor, the second fluid path defining a path internal pressure;
    a third fluid path coupled to the filter and connected to the second fluid path, bypassing the flow restrictor; and
    a means for controlling an input response to a valve in the third fluid path, wherein the input response either selectively obstructs or permits flow in the third fluid path.

20. The vacuum surge suppressor of claim 19 wherein the means for controlling the input response is either by way of human control input or by way of the path internal pressure.

* * * * *